(12) United States Patent
Foster

(10) Patent No.: US 7,419,108 B2
(45) Date of Patent: Sep. 2, 2008

(54) CORN FRACTIONATION PROCESS

(76) Inventor: Glen Foster, 475 Dovercourt Drive, Winnipeg, Manitoba (CA) R3Y 1G4

( * ) Notice: Subject to any disclaimer, the term of this patent is extended or adjusted under 35 U.S.C. 154(b) by 277 days.

(21) Appl. No.: 10/581,711

(22) PCT Filed: Feb. 7, 2006

(86) PCT No.: PCT/CA2006/000148

§ 371 (c)(1),
(2), (4) Date: Jun. 5, 2006

(87) PCT Pub. No.: WO2006/081673

PCT Pub. Date: Aug. 10, 2006

(65) Prior Publication Data

US 2008/0121742 A1    May 29, 2008

Related U.S. Application Data

(60) Provisional application No. 60/649,970, filed on Feb. 7, 2005.

(51) Int. Cl.
*B02C 9/04* (2006.01)
(52) U.S. Cl. .................. 241/7; 241/8; 241/10; 241/29; 241/79.1; 241/152.2
(58) Field of Classification Search ............... 241/6–13, 241/29, 79.1, 152.2
See application file for complete search history.

(56) References Cited

U.S. PATENT DOCUMENTS

| 3,979,375 | A | | 9/1976 | Rao et al. |
| 4,189,503 | A | | 2/1980 | Giguere |
| 5,250,313 | A | | 10/1993 | Giguere |
| 7,104,479 | B1 | * | 9/2006 | Griebat et al. .................. 241/7 |
| 7,138,257 | B2 | * | 11/2006 | Galli et al. .................. 435/161 |
| 2003/0104101 | A1 | | 6/2003 | Matthews et al. |
| 2003/0232109 | A1 | | 12/2003 | Dawley |
| 2004/0043088 | A1 | | 3/2004 | Endo et al. |
| 2005/0016525 | A1 | | 1/2005 | Thorre |

FOREIGN PATENT DOCUMENTS

| EP | 1213054 | 6/2002 |
| WO | WO 03/047366 | 6/2003 |
| WO | WO03/063609 | 8/2003 |
| WO | WO 03/080775 | 10/2003 |
| WO | WO 2004/093549 | 11/2004 |

* cited by examiner

*Primary Examiner*—Mark Rosenbaum
(74) *Attorney, Agent, or Firm*—Michael R. Williams; Ryan W Dupuis; Adrian D. Battison

(57) ABSTRACT

A method of corn fractionation wherein the resulting high starch concentration endosperm is subsequently used for ethanol production or dry milling is described. The method includes: providing substantially cleaned corn kernels, tempering the corn; screen processing to properly size the corn fractions; density separation of the primary fractions; rolling and/or screening the products to produce three main fractions consisting of high starch Endosperm, high oil Germ and high fiber Bran.

13 Claims, No Drawings

CORN FRACTIONATION PROCESS

PRIOR APPLICATION INFORMATION

This application claims the benefit of U.S. Provisional Patent Application 60/649,970, filed Feb. 7, 2005.

BACKGROUND OF THE INVENTION

The corn kernel is comprised of a number of components, each being best suited for various commercial use patterns. The fibrous hard outer shell is the pericarp, commonly called the bran. The interior of the corn kernel consists of the endosperm and the germ. The germ contains a much higher percentage of protein compared to the other parts of the kernel and is the primary source of corn oil. The portion of the corn kernel which adheres to the corn cob is commonly referred to as the tip cap.

Wet corn milling processes can separate corn into the various major components of the kernel. In a wet milling process, the corn is firstly steeped in an aqueous solution to soften the kernel and then is ground and further processed to free the germ. Current technology is such that in a dry milling process, for the production of ethanol, the corn kernel is ground and is fed directly into the ethanol process with no separation of the corn kernel achieved. 100% of whole corn kernel is fed through the process in the production of ethanol.

The degree of separation of germ from endosperm that is achieved with conventional degerminating machines can cause problems in the overall milling process. For example, in certain commercial degerminators, the grain kernels are rubbed more against one another than against the metal of the machine. As a consequence, even though relatively good separation of some of the germ is achieved, a large quantity of fine material is generated which often is high in fat content since they contain fine particles of pulverized germ.

In certain prior art, the corn kernels are cleaned to remove foreign material and then fed into cracking rolls, which are typically used by dry millers to reduce the size of corn kernels. The cracked corn is cleaned (screened or sized) then certain fractions are put through another set of rollers that reduce the size again before re-cleaning. This process is very much like flour milling, and like flour milling it produces a selection of different products. Each product has varying levels of oil, starch, protein and fiber.

Ponnampalam et al (Applied Biochemistry and Biotechnology 115: 837-842) demonstrated that the removal of germ and fiber from whole corn kernels can improve the efficiency of ethanol production. The "germ and fiber removed corn" for this test was prepared by blending corn grits product together with degermed corn meal. However, this reference concludes that ethanol production from fermentation of corn, with the germ and fiber removed, offers efficiencies and would likely be economically beneficial but provides no recommendations as to how to accomplish this on a commercial scale.

Generally speaking the corn kernel is comprised of three major components, these are: 1. Endosperm—which is comprised primarily of starch. 2. Germ—which contains the bulk of the extractable corn oil and, 3. Bran—comprised mainly of the high fibre pericarp and tip cap. For the efficient production, ethanol plants require primarily starch and a small amount of protein.

There is an approximate 40% density difference between corn germ and endosperm and an approximate 75% difference in density between the bran (pericarp/tip) and germ. It is notable that as product size is reduced, the density will also change. Finely ground pericarp and tips will increase in density significantly after fine grinding. Grinding the pericarp and tips too fine results in a poor separation.

SUMMARY OF THE INVENTION

According to a first aspect of the invention, there is provided a method of fractionating corn comprising:
  a) tempering a quantity of corn kernels;
  b) cracking the corn kernels;
  c) threshing the cracked corn kernels;
  d) separating the corn particles into a first fraction which is above a threshold size and a second fraction which is below a threshold size;
  e) separating the second fraction into a large grit fraction and a medium grit fraction;
  f) gravity-separating the large grit fraction into large endosperm and large germ/pericarp/endosperm; and
  g) gravity-separating the medium grit fraction into medium endosperm and medium germ/pericarp/endosperm.

According to a second aspect of the invention, there is provided a system for fractionating a crop of interest comprising:
  a cracking unit for cracking the crop of interest into at least 3 and preferably 3-10 pieces;
  a breaking unit for threshing the crop of interest into smaller fragments;
  a first separator for separating the fragments into oversize fragments which are re-threshed and processing fragments;
  a second separator for separating the processing fragments into large fragments and medium fragments according to size and shape, as discussed above;
  a large density separator for separating the large fragments into a large heavy fraction and a large light fraction; and
  a medium density separator for separating the medium fragments into a medium heavy fraction and a medium light fraction.

DESCRIPTION OF THE PREFERRED EMBODIMENTS

Unless defined otherwise, all technical and scientific terms used herein have the same meaning as commonly understood by one of skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein is a method of corn fractionation wherein highly purified endosperm is recovered and subsequently used for ethanol production or dry milling. As discussed below, corn kernels are moisture tempered prior to cracking. The cracking step effectively fractures the majority of the corn kernels into fewer than 10 large pieces not including the particles of starch grains that may fall out. This step cracks open the hard outer shell of the kernel allowing for processing by subsequent equipment. The large fractured pieces are then threshed to further break the kernels. This material is subsequently screened which separates it into three size fractions: large grit, medium grit and fines which are then individually subjected to further separation. Specifically, the large grit and the medium grit are subjected to density separation wherein endosperm is separated from lighter fractions containing germ and pericarp as well as endosperm. There is an approximate 40% density difference between corn germ and endosperm and an approximate 75% difference in density between the bran (pericarp/tip) and germ. It is notable that as product size is reduced, the density will also change. The efficiency of the process is further improved by recovering endosperm in these lighter fractions by reducing the endosperm to flour, as discussed below. The end result is that the corn is fractionated into three highly purified fractions: endosperm, pericarp/tips and germ, as discussed below.

As will be appreciated by one of skill in the art, in some embodiments, the corn kernels are kernels which have been cleaned first to remove foreign material, for example, but by no means limited to cobs, sticks, weed seeds, rocks and the like. Typically, this is done with an aspirator and screen machine and then a destoner although other arrangements known in the art may also be used.

In some embodiments, the oversize product is removed using a scalp screen that has approximately 28/64" to 34/64" round holes The whole corn is tempered with hot water or steam. The moisture is allowed to soak into the kernel for a period of time. For example, the corn may be tempered for approximately 10 minutes, or the corn may be soaked until a moisture above 14.5% is achieved. As will be appreciated by one of skill in the art, other suitable times and moistures may be used and are within the scope of the invention. The corn is then cracked between 2 rollers with a grooved profile and equal speed. If the rolls are of unequal speed, the rollers act to tear the kernel apart, which also tears the germ apart. The rolls are grooved to cause the cracking, otherwise the rolls would just flatten the whole kernel but not crack it. Cracks are caused by point stresses (uneven pressure across a surface). This cracks the corn without tearing it apart. In this manner, the cracking rolls reduce the size of the kernels. This method has the advantages of not being horsepower intensive and not creating significant quantity of fine materials that limit the ability to accurately separate the corn components, as described below.

Typically, passing the cleaned and tempered corn kernels through the cracking rolls results in a single kernel being broken into for example, fewer than 10 large pieces as discussed above, or for example, greater than 3 large pieces or yet further between 3 to 10 large pieces, wherein large refers to particles larger than grains of endosperm. As will be appreciated by one of skill in the art and as discussed above, this process is different from grinding wherein all of the corn kernel may be ground into fine particles. It is of note that if the corn is broken more finely, this will generate a significant quantity of fines and most of the germ will also fracture into smaller pieces, thus becoming difficult to separate. As a consequence, in the described process, it is desirable to crack the corn such that 35% to 65% of the product will stay on top of a 12/64" round hole screen. The cracked corn is then aspirated to remove loose pericarp and very fine endosperm. Any aspirated materials can be recovered and further separated later in the process, as discussed below.

The aspirated material consists of a fine dust of endosperm and pieces of pericarp. This product is screened with the other aspiration discharges as discussed below to recover the endosperm.

The cracked, aspirated corn kernels are then subjected to a sifting screener which separates the largest particles from the mixture for threshing, as discussed below. Specifically, in some embodiments, the sifting screener is an 11/64" to 14/64" round hole screen. In a preferred embodiment, the sifting screener is a 12/64" round hole screen.

The largest particles, that is, the cracked and aspirated material that does not fall through the sifting screen, are passed to a breaking unit wherein the fragments are threshed. This 'threshing' breaks the germ, tip and endosperm of the kernel apart, preferably without generating a large quantity of fines. As will be appreciated by one of skill in the art, the breaking unit may be for example a thresher or a dehuller. For example, the thresher may be a rubbing device which has a rubbing action that separates the endosperm from the germ and pericarp. Preferably, the thresher has a clearance of 3/8" or more. Breakage of the kernels is controlled by the speed of the thresher. Alternatively, a dehuller, where similar abrasive type action separates the germ/endosperm and bran, may be used. The breaking unit breaks the components apart without necessarily reducing the sizes, that is, the thresher breaks the tip and pericarp off the germ rather than reducing all components as would occur with other technologies such as a roller mill. The threshed corn is then returned to the sifting screen for further separation, as discussed below. In some embodiments, occasional purging of the overs to the next screen size product is required to prevent a build up of unthreshable product. That is, after repeated threshing, some particles may remain too large for the sifting screen. These particles may be removed periodically to prevent build-up in the breaking unit.

In some embodiments, the breaking or threshing unit has a solid outer housing rather than a perforated screen as found in the prior art, so that the smaller product is retained and is threshed as well. This is in contrast with "break rollers" which reduce the size of the product by forcing the product through an adjustable gap between the rollers to reduce product size.

As discussed above, the threshed product is returned to the sifting screen and all particles retained by the sifting screen are passed to the breaking unit as discussed above. As will be appreciated by one of skill in the art, because the process is a 'continuous flow' process, the material retained by the sifting screen will include unthreshed corn kernels and threshed particles above the threshold size.

The threshed or cracked corn that is less than the threshold size of the sifting screen, for example, smaller than a 12/64" round hole, is passed onto a slotted screen, for example, a screen having slots from 4/64" to 6/64", for example, 5/64". The threshed corn particles above the threshold of the slotted screen are sent to the large grit bin for density separation, as discussed below.

The threshed corn particles that pass through the slotted screen are then passed to a fines screen, for example a screen having round holes ranging from 3/64" to 6/64", for example, 5/64" round holes. The threshed corn particles above the threshold level of the fines screen are sent to the medium size grit bin for density separation, as discussed below. As will be appreciated by one of skill in the art, the small to mid-sized fractions, that is, those particles retained by the fines screen, are composed primarily of pericarp, tips, and germ which are separated from the fine endosperm which passes through the fines screen.

The threshed corn particles which pass through the fines screen are designated the fine corn product and is ready for fermentation, as discussed below. As will be appreciated by one of skill in the art, the fine corn product or fines fraction has a consistency that is akin to flour.

The small to mid-sized fractions (pericarp, tips, germ) are separated from the fine endosperm because this product size is difficult to separate via density difference on a gravity table. As discussed above, the medium grit product is composed primarily of germ, pericarp, tips and some endosperm.

As will be appreciated by one of skill in the art, the closer the particles are in the size, the better the separation will be on a density separation. That is, the closer the particles are terms of shape and thickness, the only difference will be density, thereby allowing for the best separation, as discussed below.

As will be appreciated by one of skill in the art, the initial round hole (12/64" to 14/64" as discussed above) is just slightly larger than the size of the germ. Thus, in some embodiments, particles above a threshold size (larger than germ size) are re-threshed while particles below the threshold size (smaller than germ size) are sorted further. Anything passing through this hole will be of germ size. Particles that are retained by the screen will be germ plus endosperm, or large endosperm, or germ and pericarp. The second screen is a slot screen because most germ pieces will not pass through the slot so that pericarp and thin endosperm can be removed from the main germ stream. That is, the slot screen separates the corn particles into large grit fraction and medium grit fraction. The last screen is a 5/64 round hole which separates the floured endosperm from the pericarp and thin endosperm. That is, the fines screen separates floured endosperm from the medium grit fraction. As discussed above, the flour tends to plug the screens on both types of density separators and can also become airborne during density separation. Furthermore, as discussed herein, this product is the correct size for fermentation so it is removed as soon as possible. As discussed above, some endosperm ready for fermentation is also removed by aspiration following the cracking of the corn.

As known by one of skill in the art, a gravity table utilizes friction to walk the heavy product up the table while the light product above slides down on the bed of heavy grain due to gravity. The screens on a gravity table will typically allow fine product (especially high density fractions) to drop into the screen and plug off the machine. Tightening up the screen size to reduce this problem leads to reduced machine capacity. A Gravity Table that might do 600 bph of wheat will likely only do 100 bph of fine product (through a 5/64" round hole) like alfalfa or clover. Because of this, gravity tables are rarely used on fine product in a high volume application.

As will be known by one of skill in the art, the free flow Camas density separation machine creates a fluidized bed ideal for sorting by density. In the example provided below, the density separator is a free flow Camas density separation machine; however, as will be appreciated by one of skill in the art, any suitable density separator known in the art may be used in the method and are within the scope of the invention. The free flow Camas separator is capable of high capacity separation if there is a density difference of 10% or greater. The free flow separators introduce the feed at the high end the product falls on a porous screen that fluidizes the grain as it flows to the discharge end. The stratified grain stream has level cut plates that separate the grain into different densities. To keep the product flowing, a vertical vibration of the screen is also provided. The free flow Camas separator is not as precise for separating as is a gravity table. The free flow separator Camas can provide high capacity when there is a large density difference that would require many gravity tables in a conventional mill. A free flow separator single Camas machine can process 70 tph with only 10,000 cfm of air flow. This is in contrast with traditional gravity tables wherein it would take a minimum of 5, possibly 6 gravity tables to do 70 tph and this would require 100,000 cfm or more of air flow.

The Camas is capable of handling a high capacity of smaller product as compared to conventional gravity tables. As discussed above, density separation of the medium grit fraction and the large grit fraction respectively with a 2-channel machine both produce a heavy discharge which is endosperm. The middle fraction or rerun is re-elevated and recycled through the reclaim channel of the Camas. The light fraction is the by-product of both channels.

The free flow Camas separator has a very tightly woven wire screen that is then rolled. The screen is very tight and prevents very small particles from lodging in the screen or passing through the screen. The product slides down this very smooth screen as the air coming thru the screen stratifies the product by density. At the end of the channel there are 2 horizontal plates that separate the product into 3 fractions: a heavy fraction, a light fraction and a middle fraction that is fed back into the machine. Furthermore, the free flow Camas density separator can operate with very fine product.

Standard gravity tables are designed to reject from 3 to 5% of the incoming product and re-circulate up to 30% of the middle cut. However, in some embodiments, the grit products entering the gravity table can have from 13 up to 20% germ. For this reason, the gravity tables have to be modified to allow for early lights discharge. Depending on the manufacturer of the table there may be as many as 4 additional early lights discharges required. If the additional lights discharges are not used, the capacity and quality of the separation may decline.

As discussed above, the large grit product and the small grit product have been separated according to size and shape, as discussed below. As will be apparent to one of skill in the art, additional separation steps may be added so that the fractions are even more homogenous in terms of size and shape and are within the scope of the invention.

In both cases, following density separation of the large grit and medium grit, the heavy product is endosperm, as discussed below. The light product consists of germ, pericarp, tips and endosperm. In some cases, there is endosperm attached to the germ. As discussed below, the germ is pliable while the endosperm is brittle. Additional endosperm is recovered by taking advantage of this difference in consistency. Specifically, the light fraction is subjected to impact means, for example, a flaking roll, or similar equipment, which flatten the pliable germ but 'flour' the brittle endosperm. Similarly the bran fractions can be subjected to impact hammers or similar equipment, which flour the brittle endosperm allowing for separation from the resulting larger particles of pericarp. Examples are provided below wherein a flaking roll and impact hammers are used although as will be appreciated by one of skill in the art, other suitable impact means may be used. It is further of note that these additional recovery steps greatly improve the efficiency of the process but are not necessarily essential steps of the process.

The large grit product is passed to a density separator where the germ and any small piece of endosperm with attached pericarp/tip are separated. Following separation, the heavy product is substantially endosperm and is referred to as the large clean grit. The light product consists of germ and also some endosperm attached to pieces of pericarp. In some embodiments, the top of the kernel is often sheared off in a thin slice. This dented thin slice will also separate with the germ on a gravity table. The light fraction is passed to a flaking roll where the germ (which is pliable) is flattened and the endosperm (which is brittle) is floured or pulverized. In a preferred embodiment, the rolls are set between 30 and 45 thousandths of an inch gap. The flaking roll discharge is then screened and/or aspirated, for example, using a sieve machine and an aspirator to separate the floured, fine endosperm from the flakes of germ and to aspirate the pericarp from the germ. The floured endosperm fraction is sent to the endosperm bin. The loose pericarp is lifted in the aspirator as discussed above and is sent for further reclaiming process. The germ product is sent to the germ bin.

In a preferred embodiment, the large grit product is passed through a length separator, for example, an indent cleaner to separate the longer pieces of grit from the shorter pieces of grit prior to density separation. This process improves the density separation. Specifically, the large grit has a large variance in the length of the product. As discussed above, for this type of separation, it is important that the particles have substantially the same shape. The different lengths of product do not separate very well on a gravity table so in some embodiments the large grit is length separated on an indent cylinder machine. The shorts are sent to one gravity table and the longs are sent to a second gravity table. It is of note that indent cleaners are well known in the art. Other similar length separators known in the art wherein material of a first length is retained in the machine for a longer period of time than material of a second length may also be used. In an indent cleaner, a trough with a screw is inserted into a cylinder. The trough is held stationary while the screw and the cylinder turn. The shorter particles sit in the pocket and centrifugal force holds the particle in as long as its center is inside the edge of the half-sphere. A longer piece will topple out sooner as its center of gravity is outside the half-sphere and it will not get lifted into the trough. The screw inside the trough pushes the short particles out the end of the machine while the long particles tumble out of the end of the cylinder.

The medium grit is also sent to a density separator, and the heavy product is sent to the endosperm bin. The light product consists of some germ, but also has a significant quantity of small pericarp particles attached to small pieces of endosperm. The light product is sent to a low speed hammermill where the impact with the hammers breaks the endsoperm from the pericarp. A screen separator removes the endosperm and aspiration removes the pericarp, as discussed above, leaving primarily endosperm with only a small amount of germ.

As discussed above, throughout the process, there are aspirators and dust pickups that remove and reclaim floured endosperm and pericarp. This is collected in the dust filters. The material captured in the dust filter is screened to recover the floured endosperm. Also at the aspirators and other locations, pericarp with attached endosperm is removed. These discharges are collected and fed into a low speed hammermill, which knocks the endosperm loose as well as reduces the fiber flake size thus reducing volume and providing for more efficient storage.

The process separates corn kernels into 3 fractions: endosperm fraction, germ fraction and pericarp/tip fraction. The endosperm may be ground before it goes to process. The process may be ethanol production, low fibre/low oil animal feed, corn flour or possibly a variety of other corn products.

The Germ Fraction can be marketed as corn germ or processed to produce corn oil or bio-diesel or sold as a high fat animal feed.

The pericarp/tip fraction or bran fraction can also be further processed to be sold as a human-edible fiber. Alternatively, the fibre product can be burned on site to be utilized as an energy source, for example, for steam production. The bran product is also a highly digestible fibre. The combined product may be sold as animal feed as well.

Present whole corn feedstock typically processed in an ethanol plant has approximately 70% starch, 9% protein, 4% fat, 1% ash 9% fiber. Using the described fractionation process, the endosperm fraction will have approximately 80-90% starch, 6-10% protein, 0.5%-2.5% fat, 0.2%-0.7% ash and 4-5% fiber.

Because pericarp (fiber) and germ (oil) have been removed from the endosperm, plant operation is improved; drying costs are lowered and equipment wear is reduced. Furthermore, the process is simpler, easier to operate and requires less horsepower and capital than current methods, as discussed herein. Specifically, oil in the ethanol process plugs heat exchangers, bakes on and coats trays in the distillation columns and evaporators and it burns to produce VOC in the dryer. Oil removal via the fractionation of the corn as discussed herein prior to ethanol processing will reduce these problems.

Furthermore, increased starch concentration has the potential to improve ethanol yield and lower the operational and processing cost per liter of ethanol produced.

Reduced fiber, ash, protein and oil into the ethanol process will reduce the amount of product that needs to be dried. Dry product from the dryer will be approximately half the amount it would have been without fractionation.

Furthermore, the new distiller's dry grain plus solubles (DDGS) by-product will have a significantly higher protein content and lower fiber content. The new DDGS will likely now fit in poultry and hog feed rations at elevated inclusion rates due to the higher protein level and lower fiber level and will also have higher value for dairy rations Further processing of the germ and fiber fractions may yield higher value human edible products.

The reduction in VOC (Volatile Organic Compounds) that requires the use of thermal oxidizers will be drastically reduced due to the reduction of oil in the product requiring drying, as discussed above.

Conventional degermination requires much capital up front together with high operational costs due to the high-energy consumption and labour to operate. The conventional process requires a heated building complex because of water addition and numerous pieces of process equipment along with the process staff to operate. Conventional degerming while technically possible is very capital intensive and operationally costly in labour and energy resulting in low cost-effectiveness as a fractionation option.

In contrast, the described invention requires only 5 main categories of equipment and some support equipment to convey product to and from the main equipment.

The described invention process is simple and can be accomplished in a small non-heated building with minimal maintenance and manpower to manage.

As used herein, it is of note that "corn" may include sweet corn, maize, pop corn and the like.

It is of note that in other embodiments, a different crop is substituted for the corn, for example, but by no means limited to sorghum, rice, buckwheat, wheat, milo, lentils, peas, soybeans, and chick peas.

In these embodiments, the crop of interest is fractionated as discussed above. Specifically, the crop of interest is fractionated using a system that comprises:

a cracking unit that cracks the crop of interest into fewer than 10 large pieces;

a breaking unit that threshes the crop of interest into yet smaller fragments;

a first separator that separates the fragments into oversize fragments which are re-threshed and processing fragments;

a second separator that separates the processing fragments into large fragments and medium fragments according to size and shape, as discussed above;

a density separator that separates the large fragments into a large heavy fraction and a large light fraction; and a density separator that separates the medium fragments into a medium heavy fraction and a medium light fraction.

As will be appreciated by one of skill in the art, as discussed above, the cracking unit may be cracking rolls as described above or may be another suitable machine known in the art and as discussed above. Similarly, the breaking unit may be a thresher or a dehuller or other suitable device as discussed above depending on the crop of interest. Furthermore, the separating steps may be done using round hole screens and slotted screens as described above and having similar dimensions to those described above, bearing in mind of course the specific properties of the crop of interest.

While the preferred embodiments of the invention have been described above, it will be recognized and understood that various modifications may be made therein, and the appended claims are intended to cover all such modifications which may fall within the spirit and scope of the invention.

The invention claimed is:

1. A method of fractionating corn comprising:
   a) tempering a quantity of corn kernels;
   b) cracking the corn kernels;
   c) threshing the cracked corn kernels;
   d) separating the corn particles into a first fraction which is above a threshold size and a second fraction which is below a threshold size;
   e) separating the second fraction into a large grit fraction and a medium grit fraction;
   f) gravity-separating the large grit fraction into large endosperm and large germ/pericarp/endosperm; and
   g) gravity-separating the medium grit fraction into medium endosperm and medium germ/pericarp/endosperm.

2. The method according to claim 1 wherein the corn kernels are cleaned prior to tempering.

3. The method according to claim 1 wherein during step (b), the corn kernels are cracked into fewer than 10 large pieces.

4. The method according to claim 1 wherein the cracked corn kernels are aspirated following step (c) to remove fine endosperm particles.

5. The method according to claim 1 wherein the first fraction is returned to step (c) and re-threshed.

6. The method according to claim 1 wherein the large germ/pericarp/endosperm is subjected to impact means to reduce the endosperm to flour and the floured endosperm is recovered by aspiration.

7. The method according to claim 1 wherein the medium germ/pericarp/endosperm is subjected to impact means to reduce the endosperm to flour and the floured endosperm is recovered by aspiration.

8. The method according to claim 6 wherein the impact means is a flaking roll.

9. The method according to claim 7 wherein the impact means is a hammermill.

10. The method according to claim 1 wherein the large grit fraction is further separated by size prior to step (f).

11. The method according to claim 10 wherein the large grit fraction is separated by size using a length separator.

12. A system for fractionating a crop of interest comprising:
    a cracking unit for cracking the crop of interest into 3-10 pieces;
    a breaking unit for threshing the crop of interest into smaller fragments;
    a first separator for separating the fragments into oversize fragments which are re-threshed and processing fragments;
    a second separator for separating the processing fragments into large fragments and medium fragments according to size and shape, as discussed above;
    a large density separator for separating the large fragments into a large heavy fraction and a large light fraction; and
    a medium density separator for separating the medium fragments into a medium heavy fraction and a medium light fraction.

13. The system according to claim 12 wherein the crop of interest is selected from the group consisting of corn, sweet corn, maize, pop corn, sorghum, rice, buckwheat, wheat, milo, lentils, peas, soybeans, and chick peas.

* * * * *